United States Patent
Yang et al.

(10) Patent No.: US 9,923,241 B2
(45) Date of Patent: Mar. 20, 2018

(54) ELECTROLYTE ADDITIVE, ELECTROLYTE AND LITHIUM ION BATTERY USING THE SAME

(71) Applicants: Jiangsu Huadong Institute of Li-ion Battery Co. Ltd., Zhangjiagang (CN); Tsinghua University, Beijing (CN)

(72) Inventors: Ju-Ping Yang, Beijing (CN); Xiang-Ming He, Beijing (CN); Li Wang, Beijing (CN); Jian-Jun Li, Beijing (CN); Yu-Ming Shang, Beijing (CN); Jian Gao, Beijing (CN); Yao-Wu Wang, Beijing (CN); Jian-Wei Guo, Beijing (CN)

(73) Assignees: Jiangsu Huadong Institute of Li-ion Battery Co. Ltd., Zhangjiagang (CN); Tsinghua University, Beijing (CN)

( * ) Notice: Subject to any disclaimer, the term of this patent is extended or adjusted under 35 U.S.C. 154(b) by 206 days.

(21) Appl. No.: 14/983,501

(22) Filed: Dec. 29, 2015

(65) Prior Publication Data
US 2016/0111754 A1 Apr. 21, 2016

Related U.S. Application Data

(63) Continuation of application No. PCT/CN2014/081142, filed on Jun. 30, 2014.

(30) Foreign Application Priority Data

Jul. 12, 2013 (CN) .......................... 2013 1 0293348

(51) Int. Cl.
H01M 10/052 (2010.01)
H01M 10/0567 (2010.01)
(Continued)

(52) U.S. Cl.
CPC ....... *H01M 10/0567* (2013.01); *C07F 7/0849* (2013.01); *H01M 10/052* (2013.01);
(Continued)

(58) Field of Classification Search
CPC .................. H01M 10/0567; H01M 10/052
See application file for complete search history.

(56) References Cited

U.S. PATENT DOCUMENTS

| | | | |
|---|---|---|---|
| 4,806,608 A * | 2/1989 | Klemarczyk | ......... C07F 7/0854 526/248 |
| 2005/0019671 A1 | 1/2005 | Han et al. | |

(Continued)

FOREIGN PATENT DOCUMENTS

| | | |
|---|---|---|
| CN | 1454400 | 11/2003 |
| CN | 1577945 | 2/2005 |

(Continued)

*Primary Examiner* — Olatunji Godo

(57) ABSTRACT

The present disclosure provides an electrolyte additive. The electrolyte additive comprises: maleimide derivative, bis-maleimide derivative, or combinations there of The structural formulas of maleimide derivative and bis-maleimide derivative respectively are:

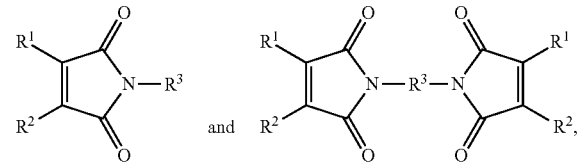

wherein, $R^1$, $R^2$ are selected from hydrogen atom and halogen atoms, $R^3$ is selected from silicon containing group, nitrogen containing group, fluorine containing group, phosphorus containing group, and a repeating ethoxy group. The (Continued)

present disclosure also provides an electrolyte liquid and a lithium ion battery using the electrolyte additive.

8 Claims, 4 Drawing Sheets

(51) Int. Cl.
  *C07F 7/08* (2006.01)
  *H01M 10/0525* (2010.01)
(52) U.S. Cl.
  CPC .... *H01M 10/0525* (2013.01); *H01M 2220/20* (2013.01); *H01M 2220/30* (2013.01)

(56) References Cited

U.S. PATENT DOCUMENTS

2008/0160418 A1* 7/2008 Pan ................... H01M 10/0525
                                                           429/328
2009/0142670 A1   6/2009 Wang et al.

FOREIGN PATENT DOCUMENTS

| CN | 101212065 | 7/2008 |
| CN | 101471456 | 7/2009 |
| CN | 103579675 | 2/2014 |
| EP | 1339127 | 8/2003 |

* cited by examiner

ELECTROLYTE ADDITIVE, ELECTROLYTE AND LITHIUM ION BATTERY USING THE SAME

CROSS-REFERENCE TO RELATED APPLICATIONS

This application claims all benefits accruing under 35 U.S.C. § 119 from China Patent Applications No. 201310293348.X, filed on Jul. 12, 2013 in the China Intellectual Property Office, the content of which is hereby incorporated by reference. This application is a continuation under 35 U.S.C. § 120 of international patent application PCT/CN2014/081142 filed Jun. 30, 2014, the content of which is hereby incorporated by reference.

FIELD

The present disclosure relates to electrolyte additives, and electrolytes and lithium ion batteries using the same.

BACKGROUND

As the developments of electric vehicles and potable electronic devices such as mobile phones, digital cameras, and laptops, the market for lithium ion batteries with high efficiency and high energy density increasingly grow. Lithium ion battery has the highest voltage and highest energy density in commercial batteries, and has good prospects for development. However, as more and more lithium ion batteries are used in electric vehicles, hybrid vehicles, wireless power tools, and military, the voltage and energy density of the lithium ion battery have higher requirements.

A lithium ion battery is composed by electrodes, separator, and electrolyte. The stability of the electrolyte is an important component in lithium ion batteries, to ensure the stable performance of the lithium ion battery. The electrochemical window of a conventional electrolyte used in the lithium ion battery only reaches about 4.5V, that is, a charging voltage higher than 4.5V causes an oxidation decomposition of the electrolyte, making the electrolyte difficult to use at higher voltages.

In prior art, there are numerous studies on adding additives in the electrolyte to improve the functions and performances. However, the conventional additives are for improving the cycling performances at high voltages and capacity retentions of the lithium ion batteries. It has not been found a report to expand the electrochemical window of the electrolyte by adding the additives.

SUMMARY

The disclosure is related to an electrolyte additive expanding the electrochemical window of the electrolyte of a lithium ion battery, and the electrolyte and lithium ion battery using the additive.

An electrolyte additive selected from maleimide derivative, bis-maleimide derivative, and combinations thereof. The structural formulas of maleimide derivative and bis-maleimide derivative respectively are represented by formula I and formula II:

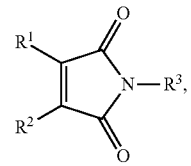

formula I

formula II wherein, $R^1$, $R^2$ are selected from hydrogen atom and halogen atoms, $R^3$ is selected from silicon containing group, nitrogen containing group, fluorine containing group, phosphorus containing group, and a repeating ethoxy group.

An electrolyte liquid includes an alkali metal salt electrolyte; a non-aqueous solvent; and the above described electrolyte additive.

A lithium ion battery includes a cathode; an anode; a separator; and the above described electrolyte liquid.

Compared to prior art, the electrolyte additive of the present disclosure only maleimide derivative, bis-maleimide derivative, or combinations thereof are added in the electrolyte, with no other additional substances, to expand the electrochemical window of the electrolyte to about 5V. Therefore, the electrolyte can be used at a higher voltage. Meanwhile, the electrolyte additive can improve the cycling performance at the higher voltage and the capacity retention of the lithium ion battery.

Figure 1:
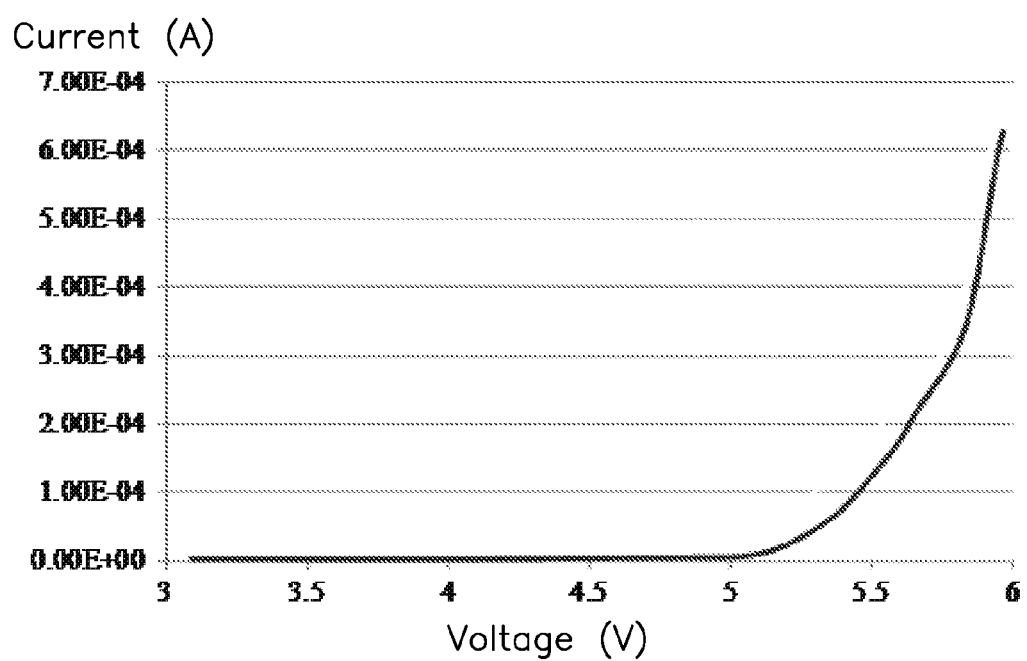
FIG. 1 is a graph showing an electrical potential scanning curve of one embodiment of an electrolyte.

A detailed description with the above drawings is made to further illustrate the present disclosure.

DETAILED DESCRIPTION

The present disclosure provides a lithium ion battery comprises a cathode, an anode, a separator, and an electrolyte liquid.

The cathode can comprise a cathode current collector and a cathode material layer located on a surface of the cathode current collector. The cathode current collector is made of aluminum, titanium, or stainless steel. The cathode material layer comprises a cathode active material, a conducting agent, and a binder. The cathode active material can be $LiCoO_2$, $LiNiO_2$, $LiFePO_4$ or other cathode active materials. The conducting agent can be carbonaceous materials, such as at least one of carbon black, conducting polymers, acetylene black, carbon fibers, carbon nanotubes, and graphite. The binder can be at least one of polyvinylidene fluoride (PVDF), polyvinylidene difluoride, polytetrafluoroethylene (PTFE), fluoro rubber, ethylene propylene diene monomer, and styrene-butadiene rubber (SBR).

The anode can comprise an anode current collector and an anode material layer located on a surface of the anode current collector. The anode current collector is made of copper, nickel, or stainless steel. The anode material layer comprises an anode active material, a conducting agent, and a binder. The cathode active material can be lithium metal, lithium inserted carbonaceous materials, or lithium alloys. The conducting agent can be carbonaceous materials, such as at least one of carbon black, conducting polymers, acetylene black, carbon fibers, carbon nanotubes, and graphite. The binder can be at least one of polyvinylidene fluoride (PVDF), polyvinylidene difluoride, polytetrafluoroethylene (PTFE), fluoro rubber, ethylene propylene diene monomer, and styrene-butadiene rubber (SBR).

The separator can be a polyolefin microporous membrane, modified polypropylene fabric, polyethylene fabric, glass fiber fabric, superfine glass fiber paper, vinylon fabric, or composite membrane of nylon fabric and wettable polyolefin microporous membrane composited by welding or bonding.

The electrolyte liquid comprises an alkali metal salt electrolyte, a non-aqueous solvent, and an electrolyte additive.

The alkali metal salt electrolyte can be $LiPF_6$, $LiBF_4$, $LiAsF_6$, $LiSbF_6$, $LiClO_4$, $LiAlCl_4$, $LiGaCl_4$, $LiNO_3$, $LiC(SO_2CF_3)_3$, $LiN(SO_2CF_3)_2$, LiSCN, $LiO_3SCF_2CF_3$, $LiC_6F_5SO_3$, $LiO_2CCF_3$, $LiSO_3F$, $Li(C_6H_5)_4$, or $LiCF_3SO_3$.

The non-aqueous solvent can be ethylene carbonate, propylene carbonate, butylene carbonate, gamma-butyrolactone, dipropyl carbonate, N-methyl pyrrolidone, N-methylformamide, N-methylacetamide, N,N-dimethylformamide, N,N-diethylformamide, acetonitrile, succinonitrile, 1,4-dicyanobutane, glutaronitrile, dimethyl sulfoxide, dimethyl sulfite, vinylene carbonate, ethylmethyl carbonate, dimethyl carbonate, diethyl carbonate, 4-fluoro-1,3-dioxolan-2-one, chloropropylene carbonate, anhydride, sulfolane, methoxymethylsulfone, tetrahydrofuran, 2-methyltetrahydrofuran, epoxy propane, methyl acetate, ethyl acetate, methyl butyrate, ethyl propionate, methyl propionate, 1,3-dioxolane, acetal, 1,2-dimethoxyethane, and 1,2-dibutyldi.

The electrolyte additive can be maleimide derivative, bis-maleimide derivative, or combinations thereof. The electrolyte additive has a mass percentage in the electrolyte liquid of 0.1%-30%. In one embodiment, the electrolyte additive has a mass percentage in the electrolyte liquid of 0.1%-10%.

The structural formulas of maleimide derivative and bis-maleimide derivative respectively are:

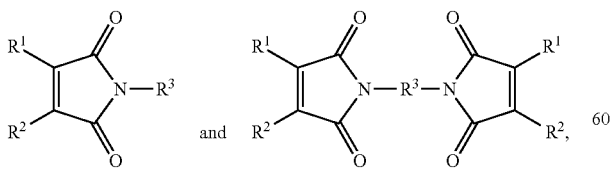

wherein, $R^1$, $R^2$ is selected from hydrogen atom and halogen atoms, $R^3$ is selected from silicon containing group, nitrogen containing group, fluorine containing group, phosphorus containing group, and a repeating ethoxy group.

The maleimide derivative can be obtained by chemically reacting 3, 4-dihalomaleic anhydride with corresponding substituted amine or hydrochloride ($R^3NH$); or can be obtained by chemically reacting N-substituted maleimide with thionyl halide (e.g., $SOBr_2$, $SOCl_2$, or $SOI_2$). Other methods can be used to obtain the maleimide derivative.

The bis-maleimide derivative can be obtained by mixing toluene, dichloroethane, and N-methyl pyrrolidone (NMP) to form a mixed solvent, and using sodium p-toluenesulfonate as a dehydrating agent to dehydrating and cyclizing at a relatively high temperature to form the bis-maleimide derivative. The bis-maleimide derivative can also be obtained by using sodium acetate or nickel acetate as a catalyst to react diamine with methyl acrylate (MA) in a solvent to form BMIA first; and then using the acetic anhydride as the dehydrating agent to dehydrate and cyclizing the BMIA to form the bis-maleimide. The bis-maleimide derivative can also be obtained by other methods.

The silicon containing group can be

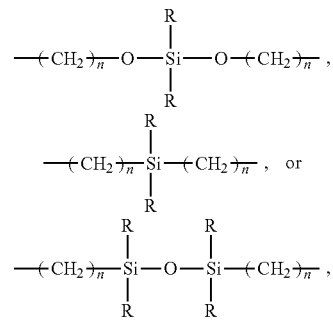

wherein R can be alkyl, n is an integer that is larger than or equal to 3 and smaller than or equal to 8.

The nitrogen containing group can be —R'OOCHN—R'—NH—COOR'—, wherein R' can be alkylene.

The fluorine containing group can be

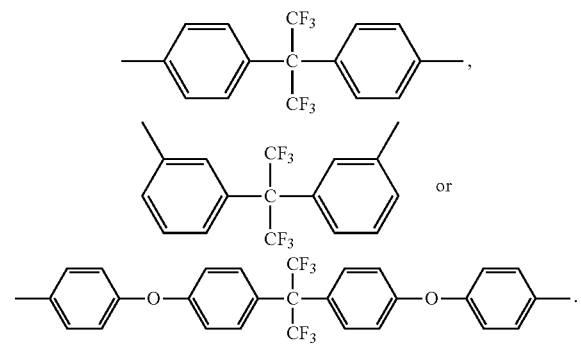

The fluorine containing group can be

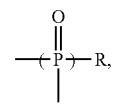

wherein R can be alkyl.

The repeating ethoxy group is ─(CH$_2$CH$_2$O)$_n$─, wherein n is an integer that is larger than or equal to 1 and smaller than or equal to 30.

EXAMPLE 1.0 mol/L of LiPF$_6$ is dissolved in a solvent mixture of ethylene carbonate (EC), diethyl carbonate (DEC), ethylmethyl carbonate (EMC) (with a volume ratio of EC/DEC/EMC=1/1/1), and 1% (mass percentage) of

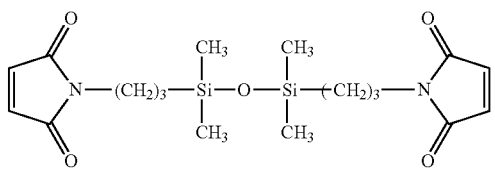

is added. Then the mixture is uniformly stirred and defoamed, to achieve the electrolyte liquid. The electrolyte liquid is injected in the lithium ion battery having the LiCoO$_2$ as the cathode active material, metal Li as the anode active material, assembled with the separator.

FIG. 1 illustrates a linear electrical potential scanning curve of the EXAMPLE obtained by using a linear potential scanning method. It can be seen from FIG. 1 that the electrochemical window of the electrolyte of the EXAMPLE is about 5V, which is larger than that of the conventional electrolyte, which is about 4.5V.

Figure 2:
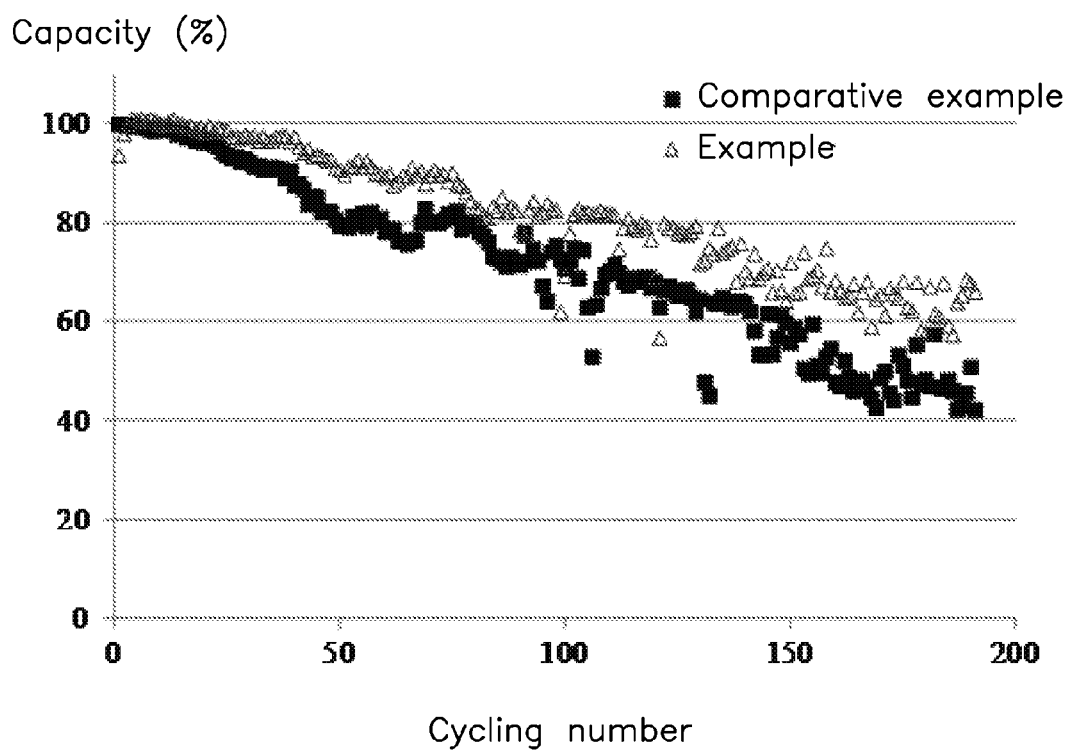
FIG. 2 is a graph comparing charge and discharge cycling performances of one embodiment and one comparative example of lithium ion batteries.

FIG. 2 illustrates a graph comparing charge and discharge cycling performances of the EXAMPLE and a comparative example of the lithium ion battery without the electrolyte additive. The charge and discharge conditions are: at 25° C., charge and discharge the lithium ion batteries at 0.2 C current rate, between 2.75V and 4.5V. It can be seen from FIG. 2 that the capacity is more stable by having the electrolyte additive in the lithium ion battery, and the lithium ion battery has a higher capacity retention.

Figure 3:
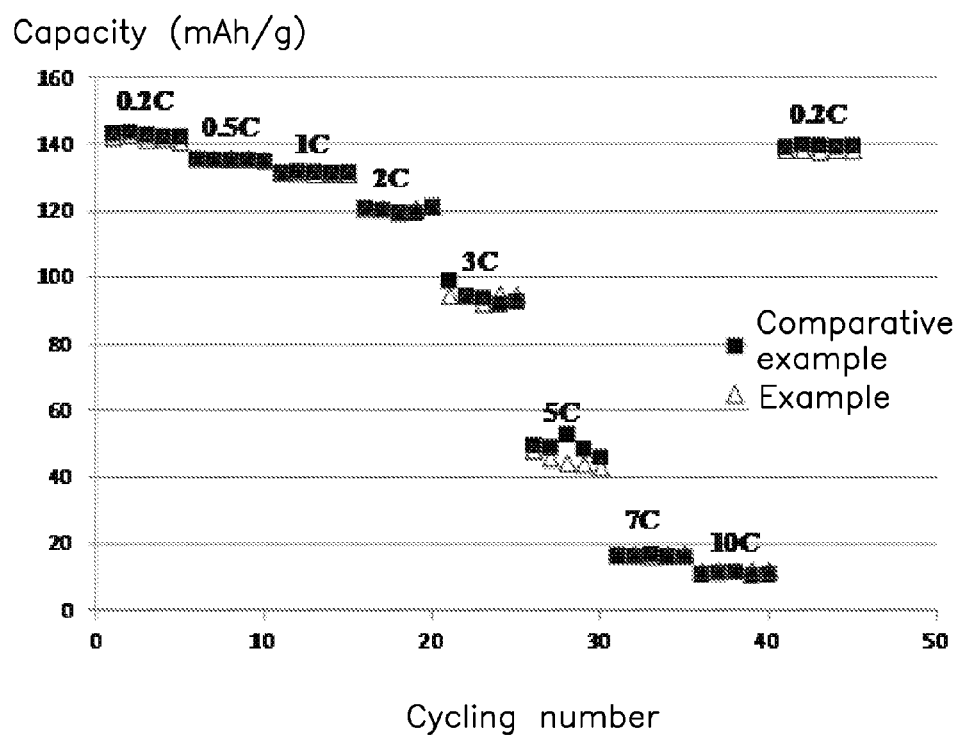
FIG. 3 is a graph showing discharge capacities at different discharge currents of one embodiment and one comparative example of lithium ion batteries.

FIG. 3 illustrates a graph showing discharge capacities at different discharge currents of the EXAMPLE and the comparative example without the additive of lithium ion batteries. The charge and discharge conditions are: at 25° C., the lithium ion batteries are charged to 4.2 V by using a 0.2 C current rate, then allowed to rest for 10 min, and then respectively discharge to 2.75V by using current rates of 0.2 C, 0.5 C, 1 C, 3 C, 3 C, 5 C, 7 C, 10 C (5 cycles for each rates). The discharge specific capacities are recorded. FIG. 3 illustrates as the current increases, both of the lithium ion batteries with or without the additive in the electrolyte liquid have discharge specific capacities decreased. No obvious difference is observed in the discharge specific capacity between the lithium ion batteries with or without the additive in the electrolyte liquid at each current. Therefore, while the capacity retention increases, the additive added in the electrolyte liquid does not decrease the rating performance of the lithium ion battery.

Figure 4:
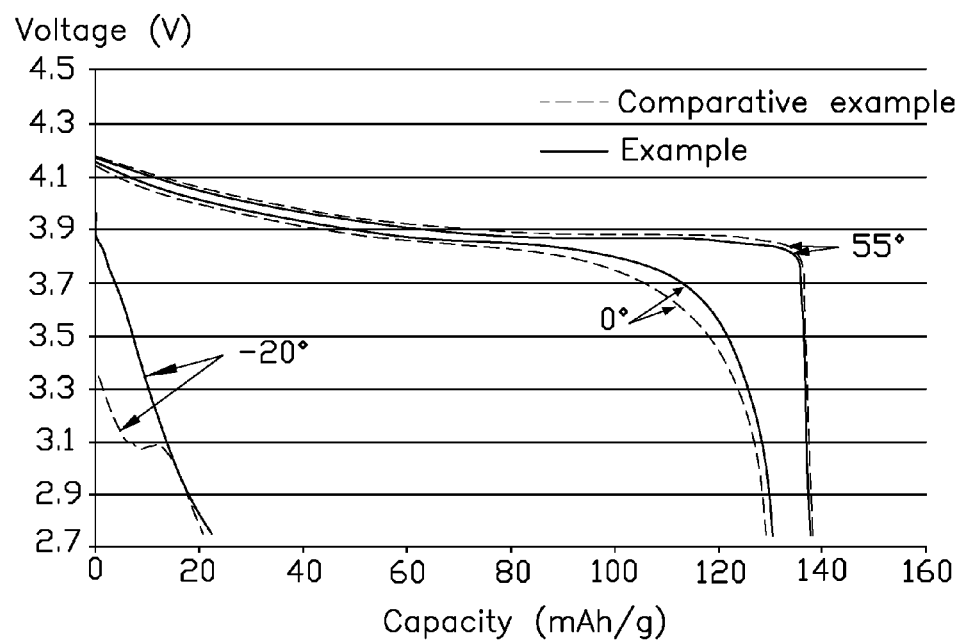
FIG. 4 is a graph showing discharge curves at different temperatures of one embodiment and one comparative example of lithium ion batteries.

FIG. 4 illustrates discharge curves at different temperatures of both of the lithium ion batteries with or without the additive in the electrolyte liquid. The charge and discharge conditions are: at 25° C., the lithium ion batteries are charged to 4.2V by using a 0.2 C current rate, then allowed to rest for 10 minutes, and respectively discharge to 2.75V at 55° C., 0° C., and −20° C. by using the 0.2 C current rate. The discharge specific capacities are recorded. FIG. 4 illustrates as the temperature decreases, the discharge specific capacities of the lithium ion batteries with or without the additive in the electrolyte liquid both decrease. No obvious difference of the discharge specific capacity is observed between the lithium ion batteries having or without the additive in the electrolyte liquid at each temperature. Therefore, the lithium ion batteries with or without the additive in the electrolyte liquid can work normally in the range of −20° C.-55 ° C.

The electrolyte additive of the present disclosure can expand the electrochemical window to 5V for the electrolyte, which makes the electrolyte capable of being used at a higher voltage. The electrolyte additive can increase the cycling performance at a higher voltage and the capacity retention of the lithium ion battery. In addition, the electrolyte additive does not decrease the rating performance of the lithium ion battery at different currents and different temperatures. The lithium ion battery using the electrolyte additive of the present disclosure can work normally in the range of −20° C.-55° C.

Additionally, one of ordinary skill in the art can make changes in spirit of the present disclosure, of course, these changes according to the spirit of the present disclosure should be included in the claimed protection scope of the present disclosure.

What is claimed is:

1. An electrolyte additive being bis-maleimide derivative, wherein a structural formula of the bis-maleimide derivative is:

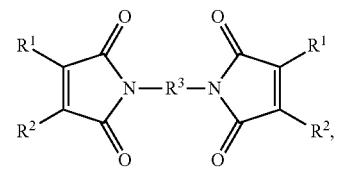

wherein, R$^1$, R$^2$ are selected from hydrogen atom and halogen atoms,

R$^3$ is selected from the group consisting of a silicon containing group, a nitrogen containing group, and a fluorine containing group, the silicon containing group is selected from the group consisting of

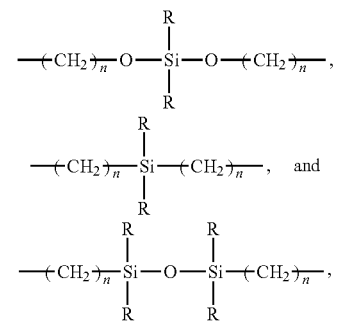

wherein R is an alkyl, and n is an integer that is larger than or equal to 3 and smaller than or equal to 8;

the nitrogen containing group is —R'OOCHN—R'—NH—COOR'—, wherein R' is an alkylene;

the fluorine containing group is selected from the group consisting of

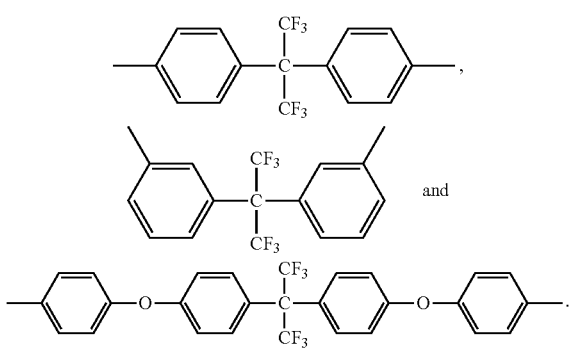

2. An electrolyte liquid comprising:
an alkali metal salt electrolyte;
a non-aqueous solvent; and
an electrolyte additive being bis-maleimide derivative, wherein a structural formula of the bis-maleimide derivative is:

wherein, $R^1$, $R^2$ are selected from hydrogen atom and halogen atoms,
$R^3$ is selected from the group consisting of a silicon containing group, a nitrogen containing group, and a fluorine containing group,
the silicon containing group is selected from the group consisting of

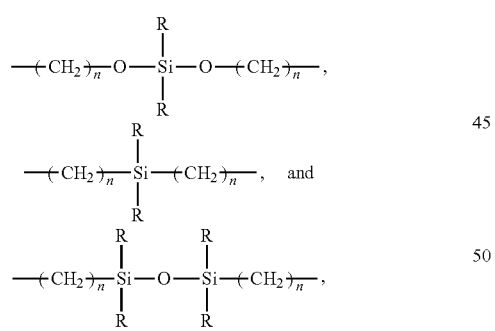

wherein R is an alkyl, and n is an integer that is larger than or equal to 3 and smaller than or equal to 8;
the nitrogen containing group is —ROOCHN—R—NH—COOR—, wherein R' is an alkylene;
the fluorine containing group is selected from the group consisting of

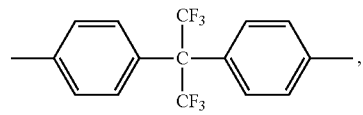

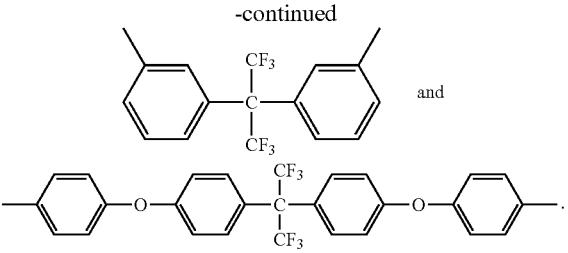

3. The electrolyte liquid of claim 2, wherein the electrolyte additive has a mass percentage of 0.1%-30%.

4. The electrolyte liquid of claim 2, wherein the electrolyte additive has a mass percentage of 0.1%-10%.

5. A lithium ion battery comprising:
a cathode;
an anode;
a separator; and
an electrolyte liquid comprising:
an alkali metal salt electrolyte;
a non-aqueous solvent; and
an electrolyte additive being bis-maleimide derivative, wherein a structural formula of the bis-maleimide derivative is:

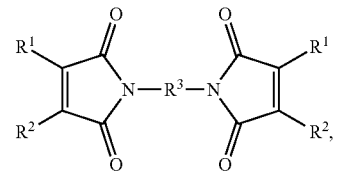

wherein, $R^1$, $R^2$ are selected from hydrogen atom and halogen atoms, $R^3$ is selected from the group consisting of a silicon containing group, a nitrogen containing group, and a fluorine containing group
the silicon containing group is selected from the group consisting of

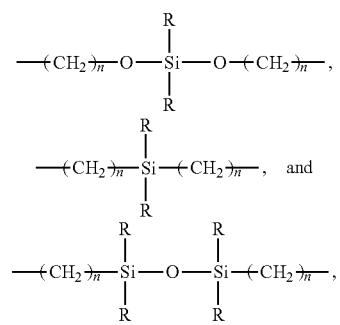

wherein R is an alkyl, and n is an integer that is larger than or equal to 3 and smaller than or equal to 8;
the nitrogen containing group is —ROOCHN—R—NH—COOR—, wherein R' is an alkylene;
the fluorine containing group is selected from the group consisting of

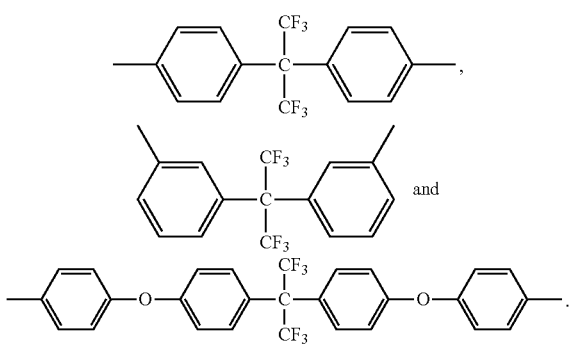

6. The electrolyte additive of claim 1, wherein $R^3$ is selected from the group consisting of a silicon containing group and a fluorine containing group, the silicon containing group is selected from the group consisting of

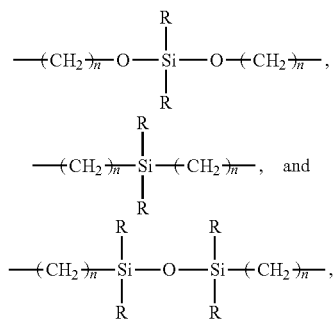

wherein R is an alkyl, and n is an integer that is larger than or equal to 3 and smaller than or equal to 8;

the fluorine containing group is selected from the group consisting of

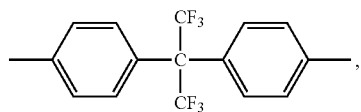

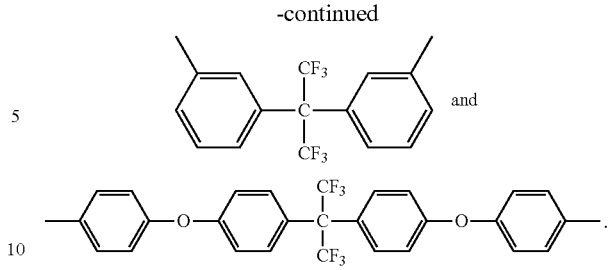

7. The electrolyte additive of claim 1, wherein $R^3$ is selected from the group consisting of

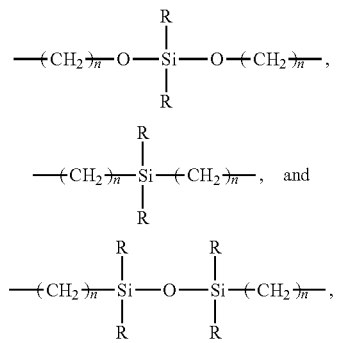

wherein R is an alkyl, and n is an integer that is larger than or equal to 3 and smaller than or equal to 8.

8. The electrolyte additive of claim 1, wherein $R^3$ is

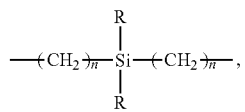

wherein R is an alkyl, and n is an integer that is larger than or equal to 3 and smaller than or equal to 8.

* * * * *